(12) United States Patent
Richardson (10) Patent No.: US 8,007,453 B2
(45) Date of Patent: Aug. 30, 2011

(54) PELVIC BRACE AND COLLAPSIBLE STRETCHER

(76) Inventor: Martin Richardson, Richmond (AU)

( * ) Notice: Subject to any disclaimer, the term of this patent is extended or adjusted under 35 U.S.C. 154(b) by 678 days.

(21) Appl. No.: 11/913,499

(22) PCT Filed: May 2, 2006

(86) PCT No.: PCT/AU2006/000573
§ 371 (c)(1),
(2), (4) Date: Jun. 5, 2008

(87) PCT Pub. No.: WO2006/116811
PCT Pub. Date: Nov. 9, 2006

(65) Prior Publication Data
US 2008/0251087 A1 Oct. 16, 2008

(30) Foreign Application Priority Data
May 2, 2005 (AU) .................. 2005902215

(51) Int. Cl.
*A61F 13/00* (2006.01)
*A61F 5/37* (2006.01)
(52) U.S. Cl. ............... 602/19; 128/846; 128/870
(58) Field of Classification Search .......... 602/19, 602/24, 60–64; 128/96.1, 100.1, 101.1, 845, 128/846, 876
See application file for complete search history.

(56) References Cited

U.S. PATENT DOCUMENTS

| 4,211,218 | A | * | 7/1980 | Kendrick | 602/19 |
| 4,580,555 | A | * | 4/1986 | Coppess | 602/23 |
| 4,665,908 | A | * | 5/1987 | Calkin | 128/870 |
| 5,928,175 | A | * | 7/1999 | Tanaka | 602/75 |
| 6,500,137 | B1 | | 12/2002 | Rebarber et al. | |
| 2006/0135898 | A1 | * | 6/2006 | Richardson | 602/19 |

FOREIGN PATENT DOCUMENTS

| GB | 1 599 664 | 10/1981 |
| NL | 1004821 | 8/1998 |
| WO | WO 01/03627 A1 | 1/2001 |
| WO | WO 01/37764 A1 | 5/2001 |
| WO | WO 03/075817 A1 | 9/2003 |
| WO | WO 2004/045471 A1 | 6/2004 |

* cited by examiner

*Primary Examiner* — Kim M Lewis
(74) *Attorney, Agent, or Firm* — Merchant & Gould P.C.

(57) ABSTRACT

The present invention relates to a device that can be used to brace the pelvic region of a patient and to a stretcher for bracing the pelvic region of a patient. The pelvic brace includes a plurality of bracing elements that can at least in part be wrapped around or about the pelvic region of a patient. The bracing elements being configured so as to be able to adjustable in length by two different fasteners so that the bracing elements can be fitted to people of various sizes ranging from young children to large adults. The stretcher includes a retractable frame assembly and preferably one or more than one pelvic brace fitted to the frame assembly to applying pressure to the pelvic region of a patient on the stretcher.

22 Claims, 7 Drawing Sheets

PELVIC BRACE AND COLLAPSIBLE STRETCHER

FIELD OF THE PRESENT INVENTION

The present invention relates to a device that can be used for bracing on splinting various parts of a patient's body such as, but not limited to, the pelvic region of a patient. According to a preferred form of the invention, one or more of the devices can also be used in a stretcher for carrying a patient.

BACKGROUND OF THE PRESENT INVENTION

One of the possible consequences of a patient sustaining a broken pelvis is that up to 3 to 6 litres of blood can be lost through internal bleeding which is a serious life threatening condition. It is known that the amount of internal bleeding can be limited by tamponading fractured pelvic bones which can be carried out by paramedics, first aiders, and surgeons through the use of pelvic braces.

In my earlier International application, namely PCT/AU2003/01501 (WO 04/045471) the full contents of which are hereby incorporated into the present specification, I describe a pelvic brace including a series of straps that are designed to allow 3 or more of the straps to be fitted around the pelvic region of a patient. In particular, during use, one of the straps may be used as an upper strap covering the upper pelvic region and another strap can be used as a lower wrap around the lower pelvic region. Depending on the height of the patient, a third strap between the upper and lower straps may also be used. An advantage provided by the device is that surgery can be performed to the pelvic region and adjoining regions of a patient by releasing one of the straps while retaining at least one other strap in position. Similarly, procedures to withdraw or supply fluids to blood vessels or bodily organs in the pelvic region are able to be performed by temporarily releasing one or more straps. Another advantage is that the straps actually utilized can be alternated or rotated and the pressure applied by each can be adjusted as the circumstances demand to provide the best possible care.

SUMMARY OF INVENTION

According to the present invention there is provided a device that can be used for bracing the pelvic region of a patient, the device including a plurality of bracing elements and one or more than one of each includes:

first and second straps, wherein the first strap is detachably connected to the second strap at a first point of interconnection that can be moved along the second strap so that the combined length of the first and second straps can be altered and thereby adjust the length of the bracing element that can be wrapped at least in part around or about the pelvic region of a patient; and attachment means that, in use, can detachably interconnect the second strap directly or indirectly to the first strap so that the bracing element forms a closed loop that can be wrapped at least in part around or about the patient, and wherein the attachment means detachably interconnects the first and second straps at a second point of interconnection that is able to be moved along the first strap so as to allow the length of the bracing element that can be wrapped around the pelvic region of a patient to be further adjusted.

An advantage provided by the device of the present invention is that it provides two means for adjusting the length of the bracing elements which enables the device to be fitted to people of various sizes ranging from young children through to large adults while maintaining an appropriate amount of pressure on the patient's pelvic region.

It will be appreciated that the first point of interconnection between the first and second straps enables the first strap to be detachably connected at desired positions along the second strap using any suitable means, such as buttons, buckles or laces. However, it is preferred that an end portion of the first strap be detachably connected to the second strap by way of hook and loop fasteners.

It is even more preferred that a moveable patch having hook or loop fasteners be sewn to the first strap and that a surface of the second strap facing outwardly when wrapped around a patient have co-operating hook and loop fasteners so that the moveable patch can be moved along and secured in position along the outside of the second strap.

It is possible that the attachment means may be in the form of a conventional buckle having a pin that is received by one of a series of holes in the first strap to secure the first strap in position. The overall length of the bracing element can be altered by changing the hole in which the pin of the buckle is located. However, it is preferred that the attachment means be in the form of a snap lock fastener having cooperating first and second parts that can be connected together when the bracing element is wrapped around the pelvic region of the patient, and one of said first and second parts can slide along the first strap to adjust the length of the bracing element. In other words, the second point of interconnect is preferably facilitated by a snap lock fastener.

It is preferred that the bracing elements also include a main panel that can be positioned on the buttock region of the patient when used for bracing the pelvic region of the patient and that said second straps be in the form of flaps attached to the main panel, and that the main panel and flaps can be at least partially wrapped around or about the pelvic region of the patient. It is preferred that the attachment means enables the first strap to be connected to the main panel by snap lock fasteners and that the first strap can slide through the snap look fastener to adjust the length of the bracing element.

It is preferred that the main panel of two or more than two bracing elements be a substantially uniform unitary panel and said second straps be in the form of two or more than two flaps that extend from the main panel.

It is also preferred that the first straps include a patch of hook and loop type fasteners that is connectable to the outer face of the second strap and/or the outer face of the main panel portion of the bracing elements. In other words, only a portion of the first strap contains hook and loop type fasteners. An advantage provided by this preferred aspect of the present invention is that it enables the device to be fitted to even a broader range of sizes of people. Connection between the main panel and the moveable patch may also be achieved by way of hook and loop fasteners.

It is even more preferred that the device have 4 bracing elements.

In the situation where the device has 4 bracing elements, it is preferred that the main panel of each bracing element be a unitary panel and that the second straps be in the form of 4 flaps that extend from the main panel.

It is also preferred that two or more of the devices may be connected together in a side-by-side arrangement to provide a larger array of bracing elements that can be used for simultaneously bracing two or more regions of a patient's body including the pelvis, legs and abdomen.

According to the present invention there is also provided a patient stretcher including a frame assembly and the bracing device having any one or a combination of the preferred features described above, whereby in use, the bracing device can be used for either bracing a region of the patient's body to tamponade broken bones or secure the patient to the stretcher.

It is preferred that the frame assembly be retractable and can be moved between a collapsed orientation and an assembled orientation. An advantage provided by this preferred aspect of the present invention is that when the retractable frame assembly is located in a collapsed orientation the frame assembly can be stored in the carry bag or back pack such as those worn by military personal during combat.

It is even more preferred that the frame assembly include telescopic members that can be moved between a retracted position when in the collapsed orientation and an extended elongate position when in the assembled orientation.

The frame assembly may also include detachable members that can be connected together to form a substantially rigid structure that can be used as a platform or base for supporting a patient. The detachable members may be in the form of two or more than two short sections that when assembled together provide that the total length of the stretcher.

Although it is possible that each bracing device may be secured to the stretchers using any suitable means, it is preferred that each bracing device include a sleeve formation in which members of the frame assembly can be located.

In the situation where the bracing elements of the device include a main panel and a plurality of flaps extending from the main panels, it is preferred that a sleeve formation be located on the main panel which forms the base or bed of the stretcher and that the elongate members are located in the sleeve.

According to the present invention there is also provided a stretcher including:
a frame assembly that is adjustable between i) a collapsed retracted orientation in which the frame assembly has a reduced length suitable for storage, and ii) an assembled elongate orientation in which the frame assembly can be used to support or carry a patient; and
a bracing assembly that is removably attached to the frame assembly, wherein the bracing assembly includes one or more than one bracing element that can at least in part be wrapped around or about the pelvic region of a patient or any other part of a patient when the bracing element is attached to the frame assembly, and wherein the bracing assembly is able to be rolled or folded on itself or about the frame assembly when in the collapsed retracted orientation.

Although it is possible that the frame assembly may include rigid planar surfaces or plates, it is preferred that the frame assembly be made from elongate members.

It is even more preferred that the frame assembly include two or more that two elongate members and that the bracing assembly include a main panel portion that spans between the elongate members and forms a base of the stretcher on which the patient can be supported.

It is preferred that the bracing assembly include a plurality of flaps extending from the main panel portion that can be wrapped at least partly around or about the pelvic region or any other part of a patient on the stretcher.

It is preferred that the bracing assembly include a strap that is detachably connected to the flap or the main panel portion at a first point of interconnection that can be moved along the flap so that the effective combined length of the main panel, flap and the strap that can at least in part be wrapped around or about the patient is able to be adjusted.

It is preferred that the bracing assembly include an attachment means that can directly or indirectly attach the strap to the main panel portion or the flap at a second point of interconnection that is able to be moved along the strap.

The bracing assembly may also include any one or more of the preferred features bracing device of the present invention described above. For example, said first and second points of interconnections of the bracing assembly may be provided by hook and loop type fasteners or snap lock fasteners, respectively as described in the context of the pelvic brace of the present invention.

BRIEF DESCRIPTION OF THE DRAWINGS

A preferred embodiment of the present invention will now be described with reference to the accompanying figures, of which.

DETAILED DESCRIPTION

The device according to the preferred embodiment of the present invention is in the form of a pelvic brace having four bracing elements which can each be separately secured in a wrapped position around the pelvic region of a patient. It is envisaged that two or more of the bracing elements can be positioned and fitted around the pelvic region of a patient so as to allow one or more of the straps to be released to facilitate surgery and repair to the pelvic region of a patient while one or more of the other straps remain in position on the patient.

Figure 1:
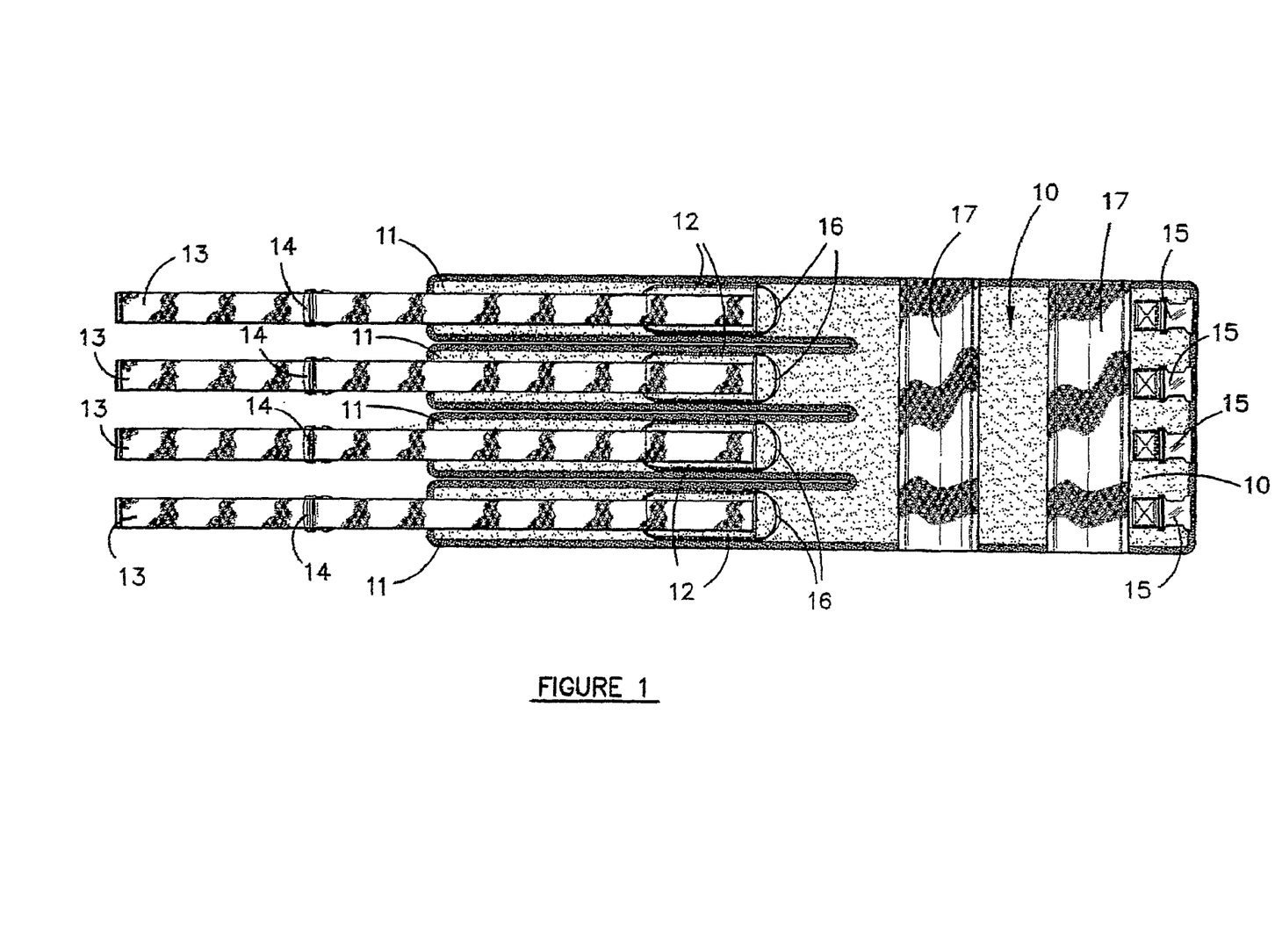
FIG. 1 is a rear view of a pelvic brace comprising a plurality of bracing elements laid out in a flat position.
Figure 2:
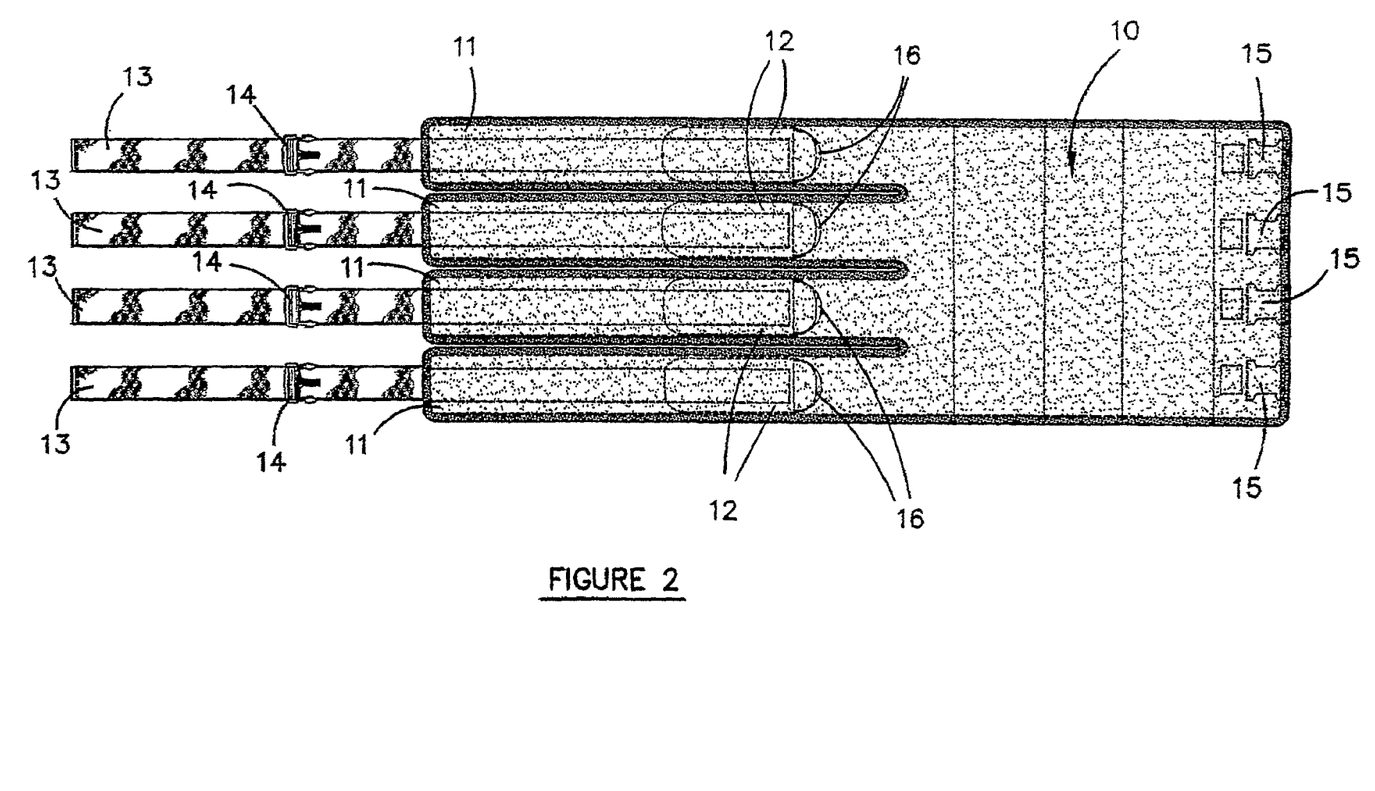
FIG. 2 is a front view of the pelvic brace shown in FIG. 1.
Figure 3:
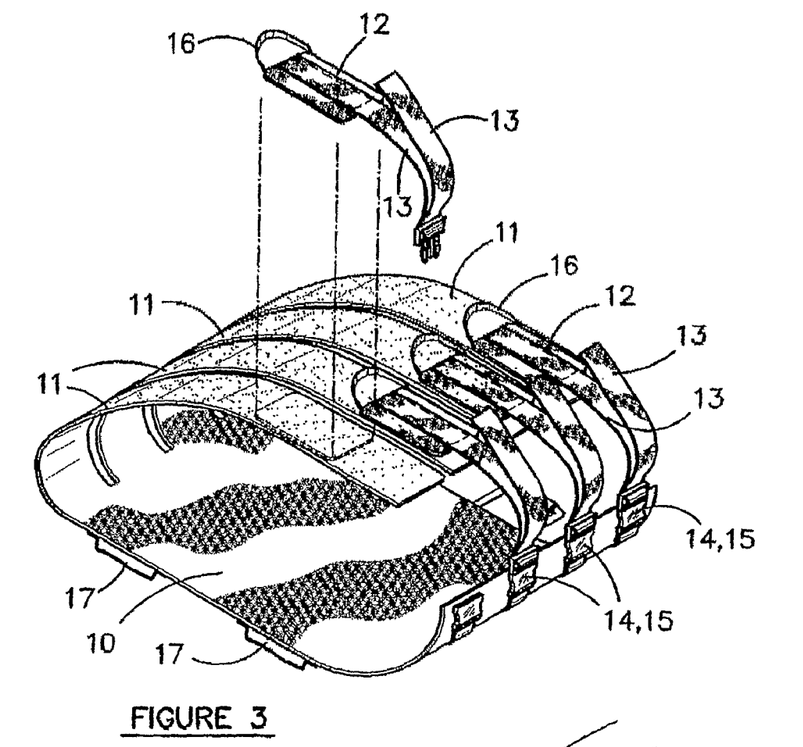
FIG. 3 is a perspective view of the pelvic brace shown in the previous Figures with three of the four bracing elements in a position as though it was being worn by a patient.
Figure 4:
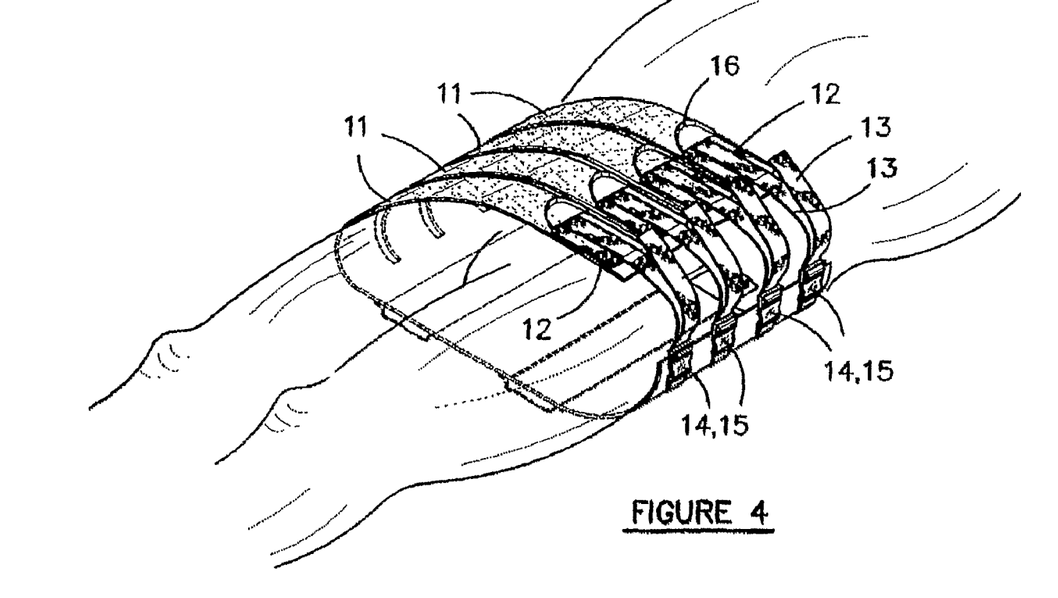
FIG. 4 is a perspective view of the pelvic brace shown in the previous Figures that is fitted to a patient.

The bracing elements are in the form of a main panel 10 the rear and front views of which are shown in FIGS. 1 and 2 and four elongated flaps 11 which extend from the main panel 10. Each bracing element also includes a removable patch 12 or foot which is shown in more detail in FIG. 5. Sewn to each removable patch 12 is a flexible strap 13 or webbing similar to the seat belt material. Each bracing element also includes a pair of cooperating male and female snap look fasteners 14 and 15 respectively. As can be seen, the female 15 component of the snap lock fastener is attached to the right hand rear face of the main panel 10 by a section of strapping or web material sewn to the rear face. The strap 13 attached to the removable patch 12 can be threaded through the male member 15 and the male member 15 can be slid along the strap 13 and held in position by virtue of the tension in the strap 13 as is common with conventional snap look fasteners.

When in use, the main panel 10 portion can be placed under the buttock region of a patient and the flaps 11 can be positioned over the patient and the snap lock fasteners 14 and 15 connected. The free end of the strap 13 can then be pulled tight so as to secure each bracing element around the pelvic region of a patient.

Figure 5:
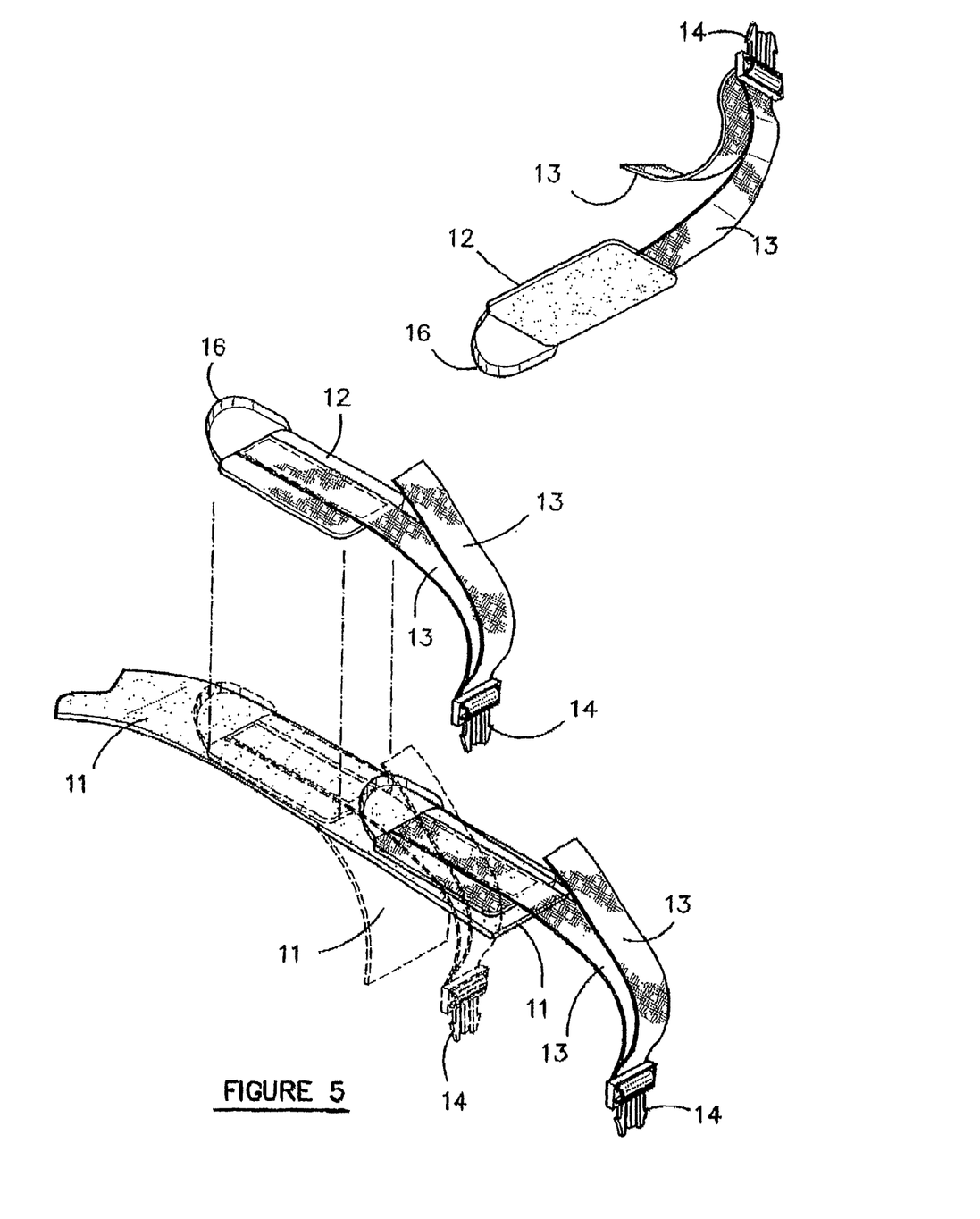
FIG. 5 is a perspective view of the pelvic brace illustrating the adjustment options of one of the bracing elements in more detail.

FIG. 5 illustrates the flap 11, removable patch 12, strap 13 and male member 14 of the snap lock fastener in more detail. In particular, in addition to sliding the male member 14 along the strap 13, the removal patch 12 can be separated from the flap 11 and moved along the length of the flap 11 and re-secured so as to enable the overall length of the bracing element that can be wrapped around a patient to be further adjusted. The underside of the removable patch 12 and the outside face of the flap 11 comprise hook and loop type fasteners. The removable patch 12 also includes a handle 16 that assists in separating the removable patch 12 from the flap 11.

An advantage provided by the preferred embodiment of the present invention is that it includes two means for adjusting the length of each bracing element that can be wrapped around the pelvic region of a patient. The preferred embodiment is therefore suitable for being fitted to people of varying sizes ranging from small children to fully grown adults.

Although not shown in the drawings, it is also possible that the removable patch 12 may also be secured to the outside face of the main panel 10 using hook and loop type fasteners. Preferably, the entire outer face of the flaps 11 and the main panel 10 contain hook and loop typo fasteners.

Figure 6:
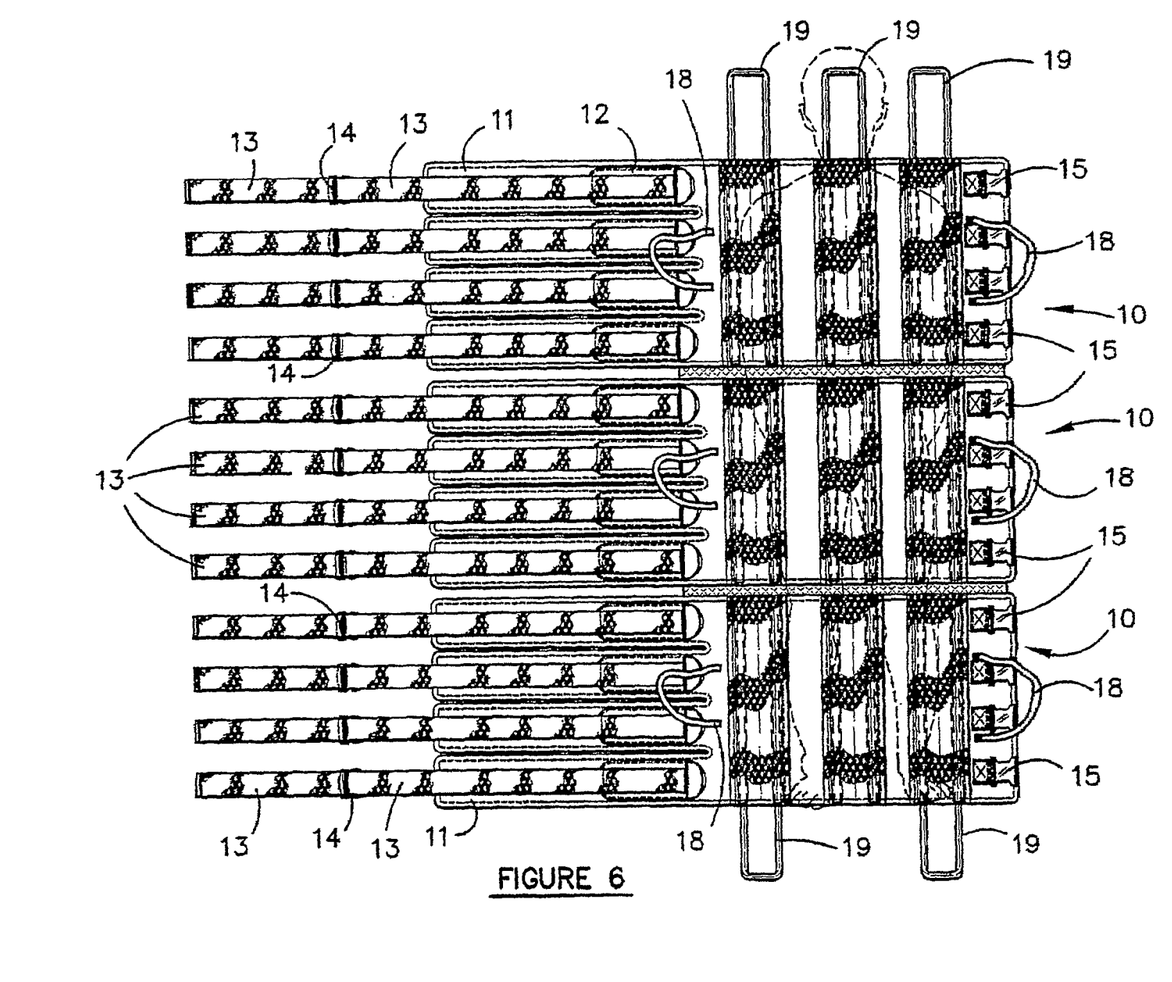
FIG. 6 is a rear view of a stretcher assembly including three of the pelvic brace devices illustrated in the previous drawings.

FIG. 6 illustrates a stretcher including a number of the pelvic braces connected side-by-side so as to form an array of bracing elements that may extend from the upper abdomen to the feet of a patient. Although not shown in detail in the Figures, the pelvic braces may be interconnected by any suitable means including zippers and shackles.

Rigidity is provided to the stretcher in a longitudinal direction by alloy members 19 that are threaded through sleeve formations 17 in the outer face of the main panel 10.

Figure 7:
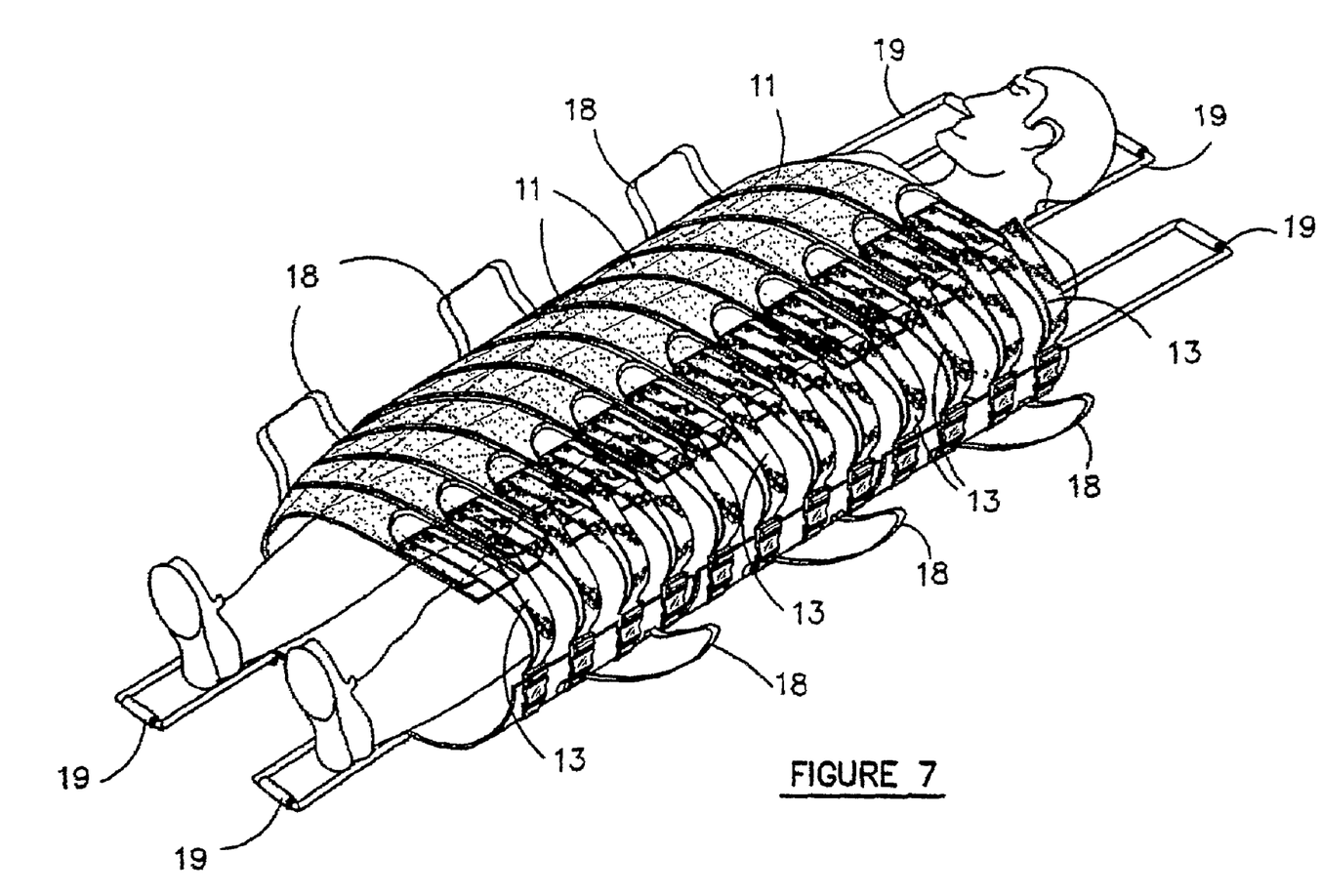
FIG. 7 is a perspective view of the stretcher assembly shown in FIG. 6 carrying a patient.

Once assembled, a patient can be placed on the inside of the main panel 10 portion and each of the bracing elements tightened to the required tension depending on the injury sustained by the patient as shown in FIG. 7. The outside of each of the bracing elements also include a pair of handles 18 to assist in carrying the stretcher.

Although not shown in the figures, it is envisaged that the alloy members 19 received by the sleeve formations 17 be telescopic so as to be able to be moved between a collapsed orientation and an extended orientation. The embodiment shown in FIGS. 6 and 7 includes three separate telescopic members 19 each in an extended orientation. In particular one of the sleeve formations 17 extends along the central region of the main panel 10 and is configured to support the patient's head. Two additional telescopic members 19 flanking the central telescopic member 19 are aligned with the hips, arms and feet of the patient.

In addition to the handles 18 attached to the outside face of the main panel, it is also possible for the stretcher to be carried by the telescopic members 19 projecting from the top and bottom of the stretcher.

Figure 8:
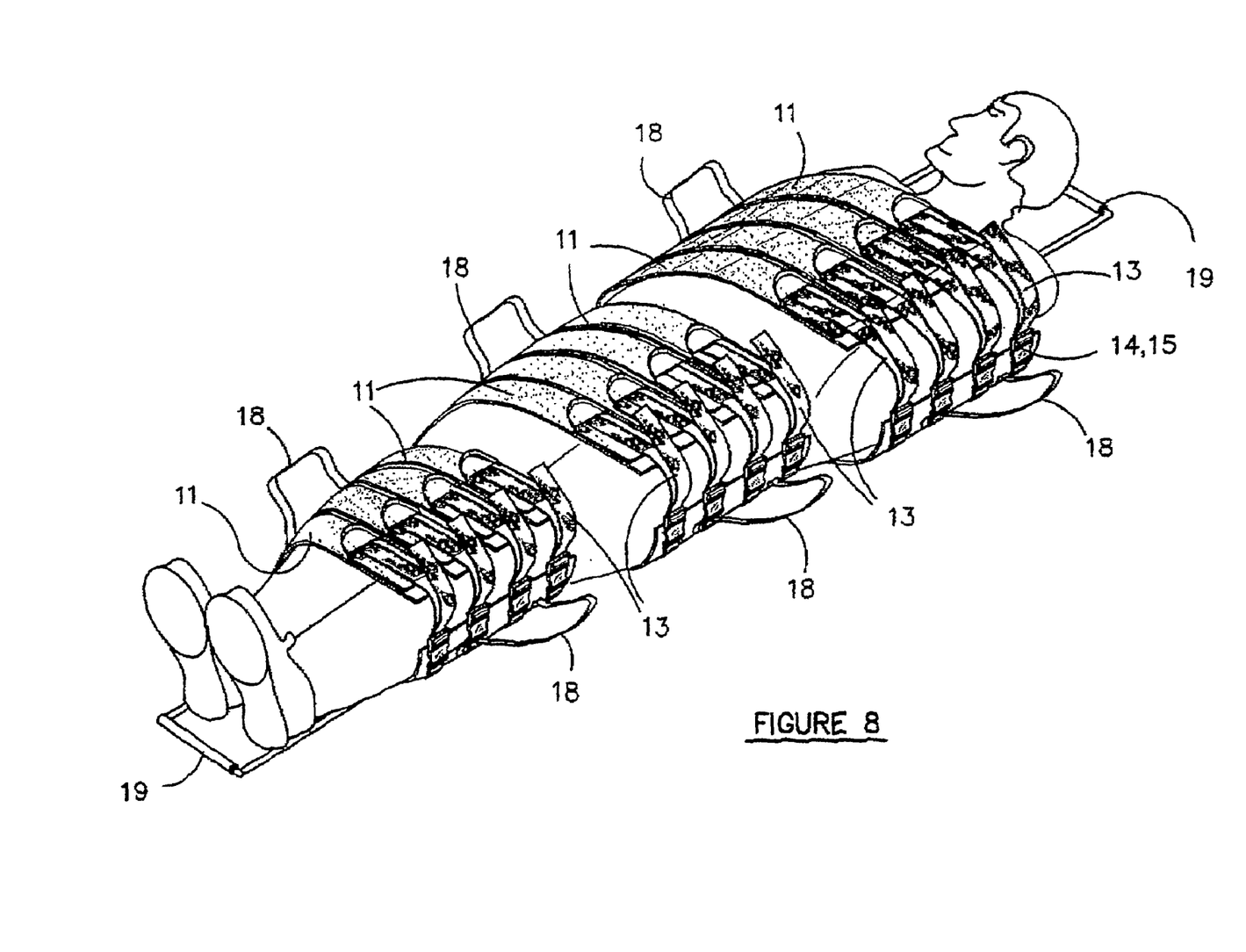
FIG. 8 is a perspective view of an alternative embodiment of a stretcher according to the present invention.

FIG. 8 illustrates an alternative stretcher comprising three of the pelvic brace devices. The stretcher shown in FIG. 8 is substantially the same as the stretcher shown in FIGS. 6 and 7 and the same reference numerals have been used to identify the same or substantially identical features. However, the stretcher shown in FIG. 8 differs from the stretcher shown in FIGS. 6 and 7 in that the three bracing devices are spaced over the height of a person and the retractable frame assembly is in the form of a single pair of telescopic members 19 rather 3 pairs of telescopic members.

It is envisaged that the stretcher according to either embodiment would be suited to applications where the patient has been injured at a remote site and emergency equipment would need to be carried in and assembled. For instance, the components of the collapsible stretcher and pelvic brace could be carried amongst a group of bush walkers or military personnel and assembled to form a stretcher when required.

It will be appreciated that many variations and modifications may be made to the embodiments described above without departing from the spirit and scope of the present invention.

For example, the pelvic brace shown in FIGS. 1 to 4 may also include handles such as handles 18 shown in FIGS. 6 to 8 to assist in carrying a patient having the brace fitted thereto.

According to an alternative embodiment of the present invention not illustrated in the Figures there is provided a pelvic brace including one or more that one adjustable strap for position over the front or other exposed region of the patient and a main panel for positioning on the buttock or a substantially unexposed region, wherein the effective length of the strap can be adjusted by way of two means. Specifically, the strap is attached to opposite sides of the main panel via fasteners, such as snap-lock fasteners, and the fasteners can be operated such that the length of strap between the fasteners can be adjusted at each point of attachment to the main panel as required. Moreover, the length of the strap between points of attachment to the main panel can be adjusted by sliding the strap through each snap-lock fastener.

The fastener may be of any suitable form including buttons, buckles, laces and hook and loop type fasteners.

In the situation where snap-lock fasteners are used, the entire strap can be separated from the brace to facilitate use of the strap. However, only one of the fasteners need be openable or releasable to allow the device to be conveniently wrapped around or about the patient without lifting the patient.

In essence, the alternative embodiment comprises a main panel or strap and an adjustable strap. The effective length of the adjustable strap is able to adjusted at the points at which the strap is attached to the main panel or the other strap.

The alternative embodiment of the present invention described in the four paragraphs immediately above may also include any one or a combination of the features of the pelvic brace described earlier in this specification.

Throughout this specification the term "strap" embraces any flexible band, web, rope, panel, main panel or alike member that can be wrapped about a patient.

The claims defining the invention are as follows:

1. A device that can be used for bracing the pelvic region of a patient, the device including a plurality of bracing elements and one or more than one of each includes:
   first and second straps, wherein the first strap is detachably connected to the second strap at a first point of interconnection that can be moved along the second strap so that the combined length of the first and second straps can be altered and thereby adjust the length of the bracing element that can be wrapped at least in part around or about the pelvic region of a patient; and
   means for attaching the second strap to the first strap configured to detachably interconnect the second strap directly or indirectly to the first strap so that the bracing element forms a closed loop that can at least partially be wrapped around or about the patient, and to detachably interconnect the first and second straps at a second point of interconnection that is able to be moved along the first strap so as to allow the length of the bracing element that can be wrapped at least in part around the pelvic region of a patient to be further adjusted.

2. The device according to claim 1, wherein the first point of interconnection between the first and second straps enables the first strap to be detachably connected at desired positions along the second strap using any one or a combination of buttons, buckles, laces, snap-lock fasteners or hook and loop fasteners.

3. The device according to claim 1, wherein the first strap includes a patch of hook and loop fasteners and that a surface of the second strap facing outwardly when wrapped around a patient has co-operating hook and loop fasteners so that the patch can be moved along and secured in position along the outside of the second strap.

4. The device according to claim 1, wherein the means for attaching the second strap to the first strap is provided by any one or a combination of buttons, buckles, laces or hook and loop fasteners.

5. The device according to claim 1, wherein the means for attaching the second strap to the first strap includes a snap lock fastener having cooperating first and second parts that can be connected together when the bracing element is wrapped at least in part around the pelvic region of the patient, and one of said first and second parts of the snap-lock fastener can slide along the first strap to adjust the length of the bracing element.

6. The device according to claim 1, wherein the bracing elements include a main panel that can be position on the buttock region of the patient when used for bracing the pelvic region of the patient and that said second straps are in the form of flaps attached to the main panel, and that the main panel and flaps can be at least partially wrapped around or about the pelvic region of the patient.

7. The device according to claim 6, wherein the main panel of two or more than two bracing elements is a unitary or single panel and said second straps are in the form of two or more than two flaps that extend from the main panel.

8. The device according to claim 6, wherein the first strap is able to be detachably connected to the second straps in the form of flaps and/or the main panel portion at said first point of interconnection.

9. The device according to claim 8, wherein the first strap is able to be detachably connected to the flaps and/or the main panel by way of hook and loop fasteners at said first point of interconnection.

10. The device according to claim 6, wherein the means for attaching the second strap to the first strap is in the form of a snap lock fastener having co-operating male and female parts, and the female part is fitted to a side of the main panel opposite to a side from which the flaps extend and the male part is slideably fitted to the first strap.

11. The device according to claim 1, wherein the device has 4 bracing elements.

12. The device according to claim 1, wherein the first and second straps are separate and unjoined.

13. A bracing assembly including two or more of the devices according to claim 1, wherein the devices are connected together in a side-by-side arrangement to provide a larger array of bracing elements that can be used for simultaneously bracing two or more regions of a patient's body including the pelvis, legs and abdomen.

14. A stretcher including a frame assembly and the bracing device according to claim 1 whereby in use, the bracing device can be used for either bracing a region of the patient's body to tamponade broken bones and/or blood vessels and/or secure the patient to the stretcher.

15. The stretcher according to claim 14, wherein the frame assembly is disassemblable and can be moved between a collapsed orientation in which the frame assembly has a reduced length and an assembled elongated orientation in which the frame assembly can be used to support or carry a patient.

16. The stretcher according to claim 14, wherein the frame assembly includes separable members that can be connected together end-to-end.

17. The stretcher according to claim 14, wherein the bracing device includes a sleeve formation.

18. A device that can be used for bracing the pelvic region of a patient, the device including:
one or more than one adjustable strap that, in use, is wrapped about and extends continuously over the frontal region of the pelvis of a patient;
a flexible bracing member that, in use, is wrapped about the buttock region of a pelvis of a patient, wherein the bracing member is directly or indirectly connected to the strap at first and second points of interconnection; and
fasteners that are located at the first and second points of interconnection and at least one of the fasteners can be released or opened to allow the strap and bracing member to be wrapping around or about a patient and closed to from a closed loop, and wherein each fastener can be operated such that the length of strap between the second and first points of interconnection can be adjusted, and thereby allow the size of the closed loop about the patient to be adjusted.

19. A device that can be used for bracing the pelvic region of a patient, the device including a plurality of bracing elements and one or more than one of each includes:
a main panel that can be positioned on the buttock region of the patient, the main panel having two or more flaps that extend therefrom;
at least two straps that are each detachably connected to one of the flaps at a first point of interconnection that can be moved along the flaps so that the combined length of the flaps can be altered and thereby adjust the effective length of the device that can be wrapped at least in part around or about the pelvic region of a patient; and
a fastener that, in use, can detachably interconnect the straps directly or indirectly to the main panel so that the device forms a closed loop that can at least partially be wrapped around or about the patient, and wherein the fastener detachably interconnects the strap to the main panel at a second point of interconnection that is able to be moved along the strap so as to allow the effective length of the device that can be wrapped at least in part around the pelvic region of a patient to be further adjusted.

20. The device according to claim 19, wherein the fasteners include any one or combination of buttons, laces, buckles, or snap-lock fasteners.

21. The device according to claim 19, wherein the first point of interconnection that enables the strap to be moved along the length of the flap includes hook and loop fasteners.

22. The device according to claim 20, wherein the first point of interconnection that enables the strap to be moved along the length of the flap includes hook and loop fasteners.

* * * * *